(12) United States Patent
Kim et al.

(10) Patent No.: US 9,169,273 B2
(45) Date of Patent: Oct. 27, 2015

(54) ABSORBENT AND PASSIVATION LAYER FOR OPTICAL ELEMENT COMPRISING THE SAME

(75) Inventors: Seok Gi Kim, Seongnam-si (KR); Young Sung Suh, Seongnam-si (KR); Kyung Keun Yoon, Seongnam-si (KR)

(73) Assignee: KOLON INDUSTRIES, INC., Gwacheon-si (KR)

( * ) Notice: Subject to any disclaimer, the term of this patent is extended or adjusted under 35 U.S.C. 154(b) by 710 days.

(21) Appl. No.: 13/391,230

(22) PCT Filed: Aug. 20, 2010

(86) PCT No.: PCT/KR2010/005560
§ 371 (c)(1),
(2), (4) Date: Jul. 5, 2012

(87) PCT Pub. No.: WO2011/021903
PCT Pub. Date: Feb. 24, 2011

(65) Prior Publication Data
US 2012/0261613 A1    Oct. 18, 2012

(30) Foreign Application Priority Data

Aug. 21, 2009  (KR) .................. 10-2009-0077688
Aug. 21, 2009  (KR) .................. 10-2009-0077692

(51) Int. Cl.
C07F 5/06 (2006.01)
B01J 20/04 (2006.01)
B01J 20/22 (2006.01)
B01J 20/28 (2006.01)
H01L 51/52 (2006.01)

(52) U.S. Cl.
CPC ............... *C07F 5/066* (2013.01); *B01J 20/041* (2013.01); *B01J 20/223* (2013.01); *B01J 20/28052* (2013.01); *H01L 51/5237* (2013.01); *H01L 2251/5315* (2013.01); *H01L 2251/5323* (2013.01); *H01L 2251/5338* (2013.01)

(58) Field of Classification Search
None
See application file for complete search history.

(56) References Cited

U.S. PATENT DOCUMENTS 6,291,699 B1 * 9/2001 Birmingham et al. ........ 556/489

* cited by examiner

*Primary Examiner* — Necholus Ogden, Jr.
(74) *Attorney, Agent, or Firm* — Sughrue Mion, PLLC

(57) ABSTRACT

This invention relates to an absorbent and a passivaton layer for an optical element including the same, which may suppress infiltration of moisture without blocking light, may be applied to flexible substrates and may prevent deterioration of optical elements thus maintaining emission properties during extended use.

16 Claims, 1 Drawing Sheet

ABSORBENT AND PASSIVATION LAYER FOR OPTICAL ELEMENT COMPRISING THE SAME

CROSS REFERENCE TO RELATED APPLICATIONS

This application is a National Stage of International Application No. PCT/KR2010/005560 filed Aug. 20, 2010, claiming priority based on Korea Patent Application No. 10-2009-0077688 filed Aug. 21, 2009 and Korea Patent Application No. 10-2009-0077692 filed Aug. 21, 2009, the contents of all of which are incorporated herein by reference in their entirety.

TECHNICAL FIELD

The present invention relates to an absorbent used in an optical element, and to a passivation layer for an optical element comprising the same.

BACKGROUND ART

Typically, light-emitting devices, which do not need an external light source and are self-luminous, are advantageous because of high light-emitting efficiency, superior luminance and viewing angles and fast response rates, but are disadvantageous because moisture or oxygen in the atmosphere infiltrates the light-emitting device and thus the electrode may be oxidized or the device itself may deteriorate, undesirably shortening the device lifetime. Hence, thorough research into the fabrication of light-emitting devices stable to moisture or oxygen is ongoing.

Also, when organic electroluminescence (EL) devices are driven for a predetermined period of time, emission properties including luminance, light-emitting efficiency and emission uniformity may more remarkably deteriorate compared to when they are initially used. The reason why the emission properties deteriorate may include for example electrode oxidation due to oxygen infiltrating the organic EL device, oxidation and decomposition of an organic material caused by heating during operation, and denaturalization of an organic material. Also, the reason why the emission properties deteriorate may further include mechanical degradation of the structure thereof. For instance, interfacial exfoliation of the structure may be caused by oxygen or moisture, and also, may result from stress induced at the interface of the structure because of respective constituents having different coefficients of thermal expansion depending on heat generated in the course of the device being driven and on heat conditions.

In order to prevent such problems, various attempts have been made to seal organic EL devices in order to inhibit contact with moisture or oxygen. For example, there is disclosed a method of preventing moisture from reaching an organic EL device by placing a sealing cap 2 having an absorbent 6 adhered to the inner wall thereof on a picture element area of an organic EL device comprising a substrate 1 and a transparent electrode 3, and an organic functional layer 4 and a metal cathode 5 which are formed on the substrate 1, filling the space therebetween with nitrogen gas 9, and then attaching the sealing cap 2 to the substrate 1 using an adhesive 7, as shown in FIG. 1.

As such, a variety of materials to use for the absorbent 6 have been studied. Particularly, thorough research into alkali earth metal oxides such as barium oxide (BaO) or calcium oxide (CaO) continues because they are able to specifically capture water molecules using a chemical reaction and do not discharge water molecules at high temperature, unlike water absorbents which physically adsorb water, such as silica gel or zeolite.

However, the absorbent 6 used is composed of inorganic compound particles and requires that a concave member be adapted to adhere to the device, undesirably making the resulting device thick.

Furthermore, because alkali earth metal oxides are opaque, they may be applied to so-called bottom emission type display devices for emitting light from the substrate 1. Whereas, in the case where alkali earth metal oxides are applied to so-called top emission type display devices for emitting light from the sealing cap 2 opposite the substrate 1, light emission may be blocked by the absorbent 6, and thus the absorbent 6 should be disposed so that it does not enter an image picture area and the mounting position should be provided.

When the absorbent is applied to top emission type display devices, for example, the use of a water absorbent comprising a polymer such as polyvinylalcohol or nylon which is transparent and is able to absorb water may be easy to conceive of. However, these polymers physically absorb water and do not have sufficient water absorption properties.

Japanese Unexamined Patent Publication No. 2001-357973 discloses the use of a particulate water absorbent disposed so as not to adversely affect light transparency in a top emission type structure, and also Japanese Unexamined Patent Publication No. 2002-56970 discloses the use of a plastic substrate in which there is dispersed a water absorbent that has particles the size of which is smaller than the light emission wavelength of organic EL devices. However, it is difficult to dispose the inorganic particles and also to uniformly disperse them as primary particles, unavoidably lowering light transparency due to the scattering of light.

Accordingly, the present invention is intended to provide an absorbent and a passivation layer for an optical element, which may prevent moisture from infiltrating an optical element.

Also, the present invention is intended to provide an absorbent and a passivation layer for an optical element, which may be applied to dual emission type display devices because of high light transmittance without blocking light.

Also, the present invention is intended to provide an absorbent and a passivation layer for an optical element, which may be applied to flexible displays.

Also, the present invention is intended to provide a passivation layer for an optical element, which may prevent an optical element from deteriorating so as to maintain emission properties during extended use.

A first preferred embodiment of the present invention provides an absorbent comprising a compound represented by Formula 1 below or a compound represented by Formula 2 below:

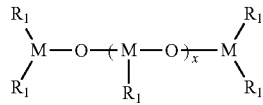

<Formula 1>

-continued

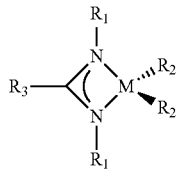
<Formula 2> wherein $R_1$, $R_2$ and $R_3$, which are the same as or different from each other, each are independently selected from among an alkyl group, a cycloalkyl group and an aryl group, M is selected from among trivalent metals, and X is an integer of 1~1000.

In this embodiment, the absorbent may have a light transmittance of 50% or more at 550 nm.

A second preferred embodiment of the present invention provides a passivation layer for an optical element, comprising a compound represented by Formula 1 below or a compound represented by Formula 2 below:

<Formula 1>

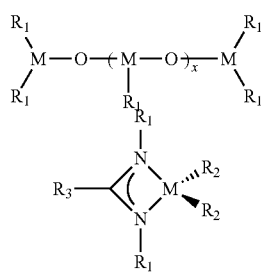

<Formula 2> wherein $R_1$, $R_2$ and $R_3$, which are the same as or different from each other, each are independently selected from among an alkyl group, a cycloalkyl group and an aryl group, M is selected from among trivalent metals, and X is an integer of 1~1000.

In this embodiment, the passivation layer for an optical element may further comprise a thermoplastic resin.

In this embodiment, the thermoplastic resin may have a moisture content of 100 ppm or less.

In this embodiment, the thermoplastic resin may have a softening point of 50~200° C.

In this embodiment, the passivation layer for an optical element may have a light transmittance of 50% or more at 550 nm.

In this embodiment, the optical element may be selected from among an organic light-emitting device (OLED), a semiconductor, a liquid crystal display (LCD), a plasma display panel (PDP), and a solar cell.

A third preferred embodiment of the present invention provides an optical element, comprising the absorbent according to the first embodiment.

A fourth preferred embodiment of the present invention provides an optical element, comprising the passivation layer according to the second embodiment.

BEST MODE

Hereinafter, a detailed description will be given of the present invention.

The present invention provides an absorbent comprising a compound represented by Formula 1 below or a compound represented by Formula 2 below.

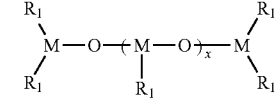
<Formula 1>

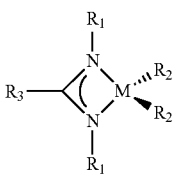
<Formula 2>

In the above formulas, $R_1$, $R_2$ and $R_3$, which are the same as or different from each other, each are independently selected from among an alkyl group, a cycloalkyl group and an aryl group, M is selected from among trivalent metals, and X is an integer of 1~1000.

As well as $R_1$, $R_2$ and $R_3$ being the same as or different from each other, two $R_1$ and $R_2$ which are located symmetrically may also be the same as or different from each other. It is particularly preferable that the two $R_1$ and $R_2$ which are located symmetrically are the same as each other for the sake of intermolecular polarity and steric hindrance.

Specific examples of the alkyl group may include methyl, ethyl, propyl, butyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl and so on.

Specific examples of the aryl group may include phenyl, tolyl, 4-cyanophenyl, biphenyl, o-, m-, p-terphenyl, naphthyl, anthranyl, phenanthrenyl, fluorenyl, 9-phenylanthranyl, 9,10-diphenylanthranyl, pyrenyl and so on.

Specific examples of the cycloalkyl group may include cyclopentyl, cyclohexyl, norbornane, adamantane, 4-methyl-cyclohexyl, 4-cyanocyclohexyl and so on.

Also, the compound represented by Formula 2 may be embodied by Formula 4 below.

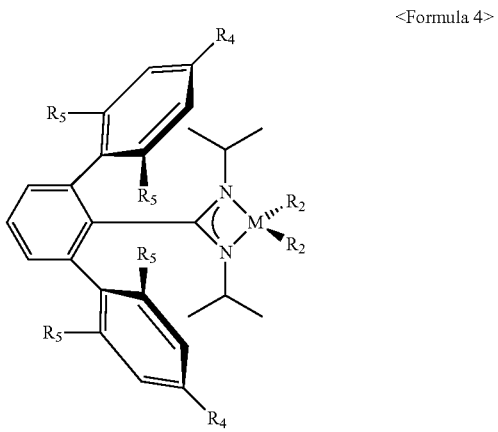
<Formula 4>

In the above formula, $R_2$, $R_4$ and $R_5$ which are the same as or different from each other are selected from among an alkyl group, a cycloalkyl group and an aryl group, and M is selected from among trivalent metals.

The compound represented by Formula 1 and the compound represented by Formula 2 may be in a liquid phase and may thus more rapidly react with moisture thereby increasing the ability to capture moisture, compared to when using conventional powdery absorbents.

Also, the compound represented by Formula 1 and the compound represented by Formula 2 may not be affected by moisture during extended use and thus may maintain stable emission properties when applied to light-emitting devices.

Furthermore, when the absorbent according to the present invention has a light transmittance of 50% or more at 550 nm, it may emit light even to an upside of the device, making it possible for it to be applied to displays such as dual emission type OLEDs.

Figure 1:
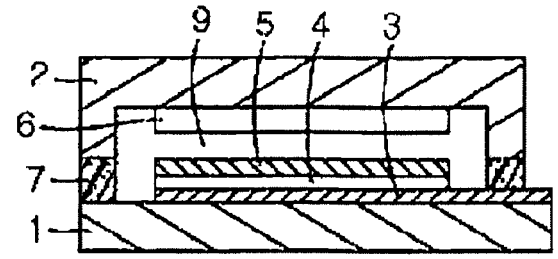
FIG. 1 is a schematic cross-sectional view showing an OLED including a conventional passivation layer for an optical element.
Figure 2:
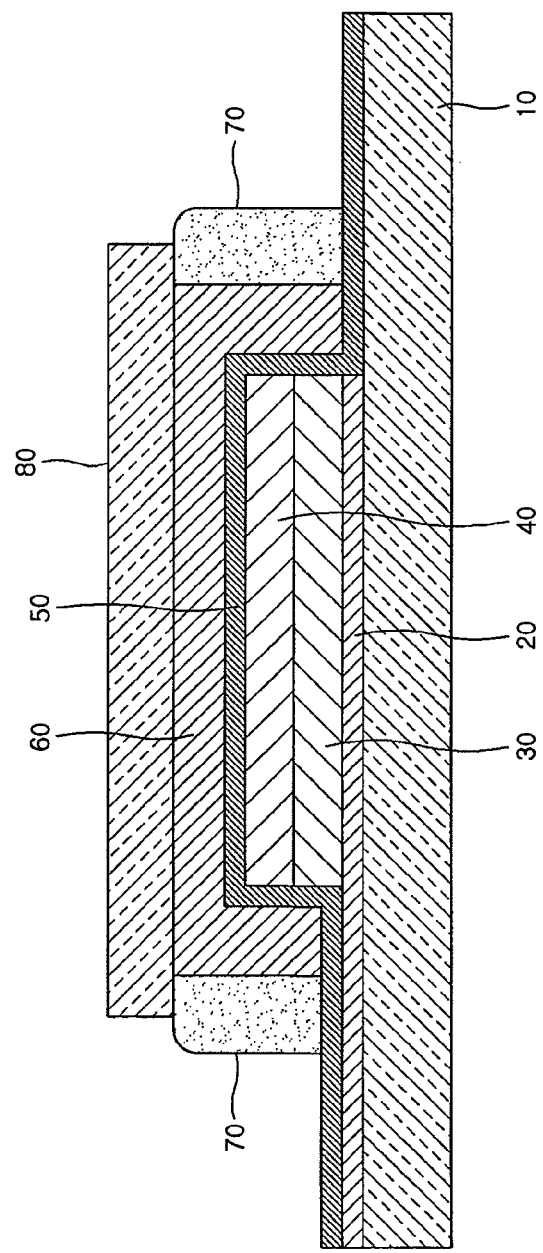
FIG. 2 is a schematic cross-sectional view showing an OLED including a passivation layer for an optical element according to an embodiment of the present invention.

In addition, the present invention provides a passivation layer for an optical element, comprising the compound represented by Formula 1 or the compound represented by Formula 2. With reference to FIG. 2, an optical element is configured such that an anode 20, an organic layer 30 and a light-transparent cathode 40 are sequentially formed on a substrate 1 and an inorganic moisture barrier layer 50 is formed thereon. Furthermore, an absorbent 60 according to the present invention is formed at a position enclosing the organic layer 30 and the cathode 40 on the inorganic moisture barrier layer 50, and a sealing substrate 80 and a UV curable seal 70 may be disposed thereon and therearound, respectively.

When the passivation layer for an optical element is formed, a mixture of the compound represented by Formula 1 or the compound represented by Formula 2 and a thermoplastic resin may be directly applied on the inorganic moisture barrier layer 50, or may be applied under the sealing substrate 80 and thus laminated with the inorganic moisture barrier layer 50. The thermoplastic resin, which is charged into the space between the element and the sealing substrate 80 so as to prevent external physical impact, may have a moisture content of 100 ppm or less and a softening point of 50~200° C. Examples of the thermoplastic resin may include EVA, PS, PP, PE, paraffin and so on.

Furthermore, when the passivation layer for an optical element has a light transmittance of 50% or more at 550 nm, it may emit light even to an upside of the device, making it possible for it to be applied to displays such as dual emission type OLEDs.

The substrate 10, the anode 20, the organic layer 30, the light-transparent cathode 40, the inorganic moisture barrier layer 50, the UV curable seal 70 and the sealing substrate 80 are not particularly limited, and known materials which are applied to OLEDs may be used.

The passivation layer for an optical element according to the present invention has a high moisture absorption rate and thus can increase the lifetime of the light-emitting device, and may also be reasonably applied to flexible displays because flexibility is prevented from decreasing.

The passivation layer according to the present invention may be applied to an encapsulation process of not only OLEDs but also semiconductors, light crystal displays (LCDs), plasma display panels (PDPs) or solar cells.

MODE FOR INVENTION

A better understanding of the present invention may be obtained via the following examples which are set forth to illustrate, but are not to be construed as limiting the present invention.

Absorbent; Compound represented by Formula 1

EXAMPLE 1

300 g of toluene (ALDRICH) was mixed with 0.2 mol weight of aluminum butoxide (ALDRICH) and 0.6 mol weight of B-locton (ALDRICH), after which the resultant mixture was strongly stirred at 800 rpm for 24 hours and then depressurized using an evaporator at 150° C. for 2 hours, thus obtaining an absorbent ($R_1$: cyclopentyl, X: 400~600, M: Al).

EXAMPLE 2

300 g of toluene was mixed with 0.2 mol weight of aluminum butoxide and 0.6 mol weight of tetrahydrophthalic anhydride (ALDRICH), after which the resultant mixture was strongly stirred at 800 rpm for 24 hours and then depressurized using an evaporator at 150° C. for 2 hours, thus obtaining an absorbent ($R_1$: phenyl, X: 400~600, M: Al).

EXAMPLE 3

300 g of toluene was mixed with 0.2 mol weight of aluminum butoxide and 0.6 mol weight of phthalic anhydride (ALDRICH), after which the resultant mixture was strongly stirred at 800 rpm for 24 hours and then depressurized using an evaporator at 150° C. for 2 hours, thus obtaining an absorbent ($R_1$: cyclohexyl, X: 400~600, M: Al).

EXAMPLE 4

300 g of toluene was mixed with 0.2 mol weight of aluminum isopropoxide (ALDRICH) and 0.6 mol weight of ethyl hexanoic acid (ALDRICH), after which the resultant mixture was strongly stirred at 800 rpm for 24 hours and then depressurized using an evaporator at 150° C. for 2 hours, thus obtaining an absorbent ($R_1$: octyl, X: 400~600, M: Al).

Absorbent; Compound represented by Formula 2

EXAMPLE 5

300 g of toluene (ALDRICH) was mixed with 0.2 mol weight of aluminum butoxide (ALDRICH) and 0.6 mol weight of piperidine propionic acid, after which the resultant mixture was strongly stirred at 800 rpm for 24 hours at 80° C. and then depressurized using an evaporator at 150° C. for 2 hours, thus obtaining an absorbent ($R_1$: hexyl, $R_2$: phenyl, $R_3$: pentyl, M: Al).

EXAMPLE 6

300 g of toluene was mixed with 0.2 mol weight of aluminum butoxide and 0.6 mol weight of N,N-diisopropyl-[2,6-bis(2,4,6-triisopropylphenyl)]-benzamidinato, after which the resultant mixture was strongly stirred at 800 rpm for 24 hours at 80° C. and then depressurized using an evaporator at 150° C. for 2 hours, thus obtaining an absorbent ($R_1$: hexyl, $R_2$: phenyl, $R_3$: phenyl, M: Al).

Passivation Layer and OLED

EXAMPLE 7

40 parts by weight of EVA (DUPONT) was dissolved in 100 parts by weight of the absorbent of Example 1 and 60 parts by weight of toluene and then mixed, after which the resultant mixture was applied to a thickness of 20 μm on a sealing substrate, allowed to stand at 90° C. for 30 min to remove the solvent and at 100° C. to soften EVA, and then laminated with an OLED.

EXAMPLE 8

100 parts by weight of the absorbent of Example 1 and 20 parts by weight of paraffin were heated to 60° C. and mixed, after which the resultant mixture was applied to a thickness of 20 μm on a sealing substrate, allowed to stand at 80° C. to soften the paraffin, and then laminated with an OLED.

EXAMPLE 9

40 parts by weight of EVA (DUPONT) was dissolved in 100 parts by weight of the absorbent of Example 5 and 60 parts by weight of toluene and then mixed, after which the resultant mixture was applied to a thickness of 20 μm on a sealing substrate (glass), allowed to stand at 90° C. for 30 min to remove the solvent and at 100° C. to soften EVA, and then laminated with an OLED.

EXAMPLE 10

100 parts by weight of the absorbent of Example 5 and 20 parts by weight of paraffin were heated to 60° C. and mixed, after which the resultant mixture was applied to a thickness of 20 μm on a sealing substrate (glass), allowed to stand at 80° C. to soften the paraffin, and then laminated with an OLED.

COMPARATIVE EXAMPLE 1

100 parts by weight of an absorbent (ALDRICH) obtained from CaO and 20 parts by weight of paraffin were heated to 60° C. and mixed, after which the resultant mixture was applied to a thickness of 20 μm on a sealing substrate, allowed to stand at 80° C. to soften the paraffin, and then laminated with an OLED.

The properties of the absorbents and OLEDs of the above examples and comparative example were measured as follows. The results are shown in Table 1 below.

The properties of the absorbent were evaluated with the solvent being removed by allowing the obtained absorbent applied to a thickness of 20 μm on the sealing substrate (glass) to stand at 90° C. for 30 min, and the device lifetime was measured using the method as described below after applying the obtained absorbent to a thickness of 20 μm on the sealing substrate (glass), allowing it to stand at 90° C. for 30 min to remove the solvent and then laminating it with the device.

(1) Moisture Absorption Rate

The absorbents and OLEDs of the above examples and comparative example were stored in a thermo-hygrostat under conditions of 25° C. RH 90%, after which the amount of absorbed moisture was measured over time and the absorption rate was calculated using Equation 1 below.

$$\text{(weight after lapse of time initial weight)/initial weight } 100 \qquad \text{<Equation 1>}$$

(2) Light Transmittance

The absorbents and OLEDs of the above examples and comparative example were stored for 2 hours in a thermo-hygrostat under conditions of 25° C. RH 90%, after which light transmittance was measured before and after absorption of moisture at 550 nm.

(3) Device Lifetime

The absorbents and OLEDs of the above examples and comparative example were stored in a thermo-hygrostat under conditions of 70° C. RH 80%, after which the time at which light intensity was reduced to 50% was measured over time.

TABLE 1

|  | Moisture Absorption Rate (%) | | | | | Light Transmittance (%) | | Device Lifetime (h) |
| --- | --- | --- | --- | --- | --- | --- | --- | --- |
|  | 30 min | 1 h | 2 h | 3 h | 4 h | Before Absorption | After Absorption |  |
| Ex. 1 | 26 | 26.8 | 27 | 27 | 27 | 98 | 97.4 | 960 |
| Ex. 2 | 12 | 14.2 | 15 | 15.2 | 15.3 | 97.6 | 92.1 | 700 |
| Ex. 3 | 23 | 24.2 | 24.8 | 25.1 | 25.1 | 93.2 | 92.6 | 760 |
| Ex. 4 | 21 | 22.6 | 23.2 | 23.3 | 23.3 | 91.4 | 88.7 | 720 |
| Ex. 5 | 32 | 34.2 | 34.8 | 34.8 | 34.8 | 88 | 87.4 | 1030 |
| Ex. 6 | 28 | 31.2 | 32.6 | 33 | 33.1 | 83.5 | 83.2 | 890 |
| Ex. 7 | 19 | 21 | 22.3 | 22.4 | 22.4 | 92.4 | 91.6 | 1100 |
| Ex. 8 | 12 | 17 | 14 | 23.5 | 23.6 | 64.1 | 63.8 | 1260 |
| Ex. 9 | 23 | 25.4 | 26 | 262 | 26.2 | 82.8 | 82.6 | 1260 |
| Ex. 10 | 20.7 | 27.2 | 31.2 | 32.4 | 32.5 | 58.1 | 57.4 | 1400 |
| C. Ex. 1 | 8 | 10 | 14 | 15 | 15 | 36.8 | 36.4 | 760 |

The invention claimed is:

1. An absorbent comprising a compound of Formula 2 below:

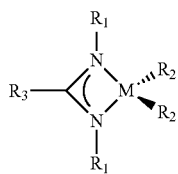

<Formula 2> wherein $R_1$, $R_2$ and $R_3$, which are same as or different from each other, each are independently selected from among an alkyl group, a cycloalkyl group and an aryl group, M is selected from among trivalent metals, and X is an integer of 1-1000.

2. The absorbent according to claim 1, which has a light transmittance of 50% or more at 550 nm.

3. A passivation layer for an optical element, comprising a compound of Formula 2 below:

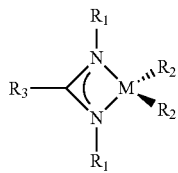

<Formula 2> wherein $R_1$, $R_2$ and $R_3$, which are same as or different from each other, each are independently selected from among an alkyl group, a cycloalkyl group and an aryl group, M is selected from among trivalent metals, and X is an integer of 1-1000.

4. The passivation layer according to claim 3, further comprising a thermoplastic resin.

5. The passivation layer according to claim 4, wherein the thermoplastic resin has a moisture content of 100 ppm or less.

6. The passivation layer according to claim 4, wherein the thermoplastic resin has a softening point of 50-200° C.

7. The passivation layer according to claim 3, which has a light transmittance of 50% or more at 550 nm.

8. The passivation layer according to claim 3, wherein the optical element is selected from the group consisting of an organic light-emitting device, a semiconductor, a liquid crystal display, a plasma display panel, and a solar cell.

9. An optical element, comprising the absorbent of claim 1.

10. An optical element, comprising the passivation layer of claim 3.

11. An optical element, comprising the absorbent of claim 2.

12. An optical element, comprising the passivation layer of claim 4.

13. An optical element, comprising the passivation layer of claim 5.

14. An optical element, comprising the passivation layer of claim 6.

15. An optical element, comprising the passivation layer of claim 7.

16. An optical element, comprising the passivation layer of claim 8.

* * * * *